(12) United States Patent
Yoshida

(10) Patent No.: US 11,406,359 B2
(45) Date of Patent: Aug. 9, 2022

(54) ULTRASOUND ENDOSCOPE AND ULTRASOUND TRANSDUCER WITH SELF-REPAIRING ACOUSTIC LENS

(71) Applicant: OLYMPUS CORPORATION, Tokyo (JP)

(72) Inventor: Satoshi Yoshida, Kawagoe (JP)

(73) Assignee: OLYMPUS CORPORATION, Tokyo (JP)

( * ) Notice: Subject to any disclaimer, the term of this patent is extended or adjusted under 35 U.S.C. 154(b) by 90 days.

(21) Appl. No.: 16/938,400

(22) Filed: Jul. 24, 2020

(65) Prior Publication Data

US 2020/0352545 A1 Nov. 12, 2020

Related U.S. Application Data

(63) Continuation of application No. PCT/JP2019/002987, filed on Jan. 29, 2019.

(30) Foreign Application Priority Data

Feb. 2, 2018 (JP) .............................. JP2018-017357

(51) Int. Cl.
*A61B 8/00* (2006.01)
*B06B 1/06* (2006.01)
(Continued)

(52) U.S. Cl.
CPC ................ *A61B 8/445* (2013.01); *A61B 8/12* (2013.01); *A61B 8/4494* (2013.01);
(Continued)

(58) Field of Classification Search
CPC ......... A61B 8/445; A61B 8/12; A61B 8/4494; A61B 8/44; B06B 1/0622; B06B 3/00;
(Continued)

(56) References Cited

U.S. PATENT DOCUMENTS 4,387,720 A * 6/1983 Miller .................... G10K 11/30
600/472
2017/0128043 A1* 5/2017 Morimoto ................ A61B 8/12
2017/0252465 A1 9/2017 Nagai et al.

FOREIGN PATENT DOCUMENTS

EP 1734066 A1 * 12/2006 ............ B01J 20/267
JP 2007-269819 A 10/2007
(Continued)

OTHER PUBLICATIONS

"Michael L. Szalai, Dominic V. McGrath, David R. Wheeler, Thomas Zifer, and James R. McElhanon, Dendrimers Based on Thermally Reversible Furan—Maleimide Diels—Alder Adducts, 2007, Macromolecules, 40(4), 818-823" (Year: 2007).*
(Continued)

*Primary Examiner* — Christopher Koharski
*Assistant Examiner* — James F McDonald
(74) *Attorney, Agent, or Firm* — Scully, Scott, Murphy & Presser, P.C.

(57) ABSTRACT

An ultrasound transducer includes: a plurality of piezoelectric devices, each of the plurality of piezoelectric devices being configured to emit an ultrasonic wave according to an electrical signal input thereto, and convert an incident ultrasonic wave from an outside into an electrical signal; and an outer surface in which a material of a scanning surface transmitting and receiving an ultrasonic wave is constituted of a self-repairing material.

13 Claims, 6 Drawing Sheets

(51) Int. Cl.
  *B06B 3/00* (2006.01)
  *G01S 7/52* (2006.01)
  *A61B 8/12* (2006.01)

(52) U.S. Cl.
  CPC .............. *B06B 1/0622* (2013.01); *B06B 3/00* (2013.01); *G01S 7/5202* (2013.01); *G01S 7/52025* (2013.01); *B06B 2201/76* (2013.01)

(58) Field of Classification Search
  CPC .............. B06B 2201/76; G01S 7/5202; G01S 7/52025; G10K 1/30; G10K 11/30; C08G 73/00; C08K 5/09
  See application file for complete search history.

(56) References Cited

FOREIGN PATENT DOCUMENTS

| | | |
|---|---|---|
| JP | 2010-213983 A | 9/2010 |
| JP | 2017-012436 A | 1/2017 |
| WO | WO 2016/088699 A1 | 6/2016 |
| WO | WO 2017/103172 A1 | 6/2017 |

OTHER PUBLICATIONS

International Search Report dated Apr. 9, 2019 issued in PCT/JP2019/002987.

* cited by examiner

ULTRASOUND ENDOSCOPE AND ULTRASOUND TRANSDUCER WITH SELF-REPAIRING ACOUSTIC LENS

This application is a continuation of PCT International Application No. PCT/JP2019/002987 filed on Jan. 29, 2019, which designates the United States, incorporated herein by reference, and which claims the benefit of priority from Japanese Patent Application No. 2018-017357, filed on Feb. 2, 2018, incorporated herein by reference.

BACKGROUND

The present disclosure relates to an ultrasound transducer and an ultrasound endoscope.

In the related art, ultrasound transducers including plural piezoelectric devices each of which emits an ultrasonic wave according to an input electrical signal, and each of which converts an incident ultrasonic wave from an external source into an electrical signal have been known (for example, JP-A-2017-012436).

In the ultrasound transducer (ultrasound probe) described in JP-A-2017-012436, a scanning surface that transmits and receives ultrasonic waves out of outer surfaces of the ultrasound transducer is constituted of an acoustic lens. The acoustic lens is generally constituted of an elastic resin or elastomer, such as silicone resin (rubber).

SUMMARY

According to one aspect of the present disclosure, there is provided an ultrasound transducer including: a plurality of piezoelectric devices, each of the plurality of piezoelectric devices being configured to emit an ultrasonic wave according to an electrical signal input thereto, and convert an incident ultrasonic wave from an outside into an electrical signal; and an outer surface in which a material of a scanning surface transmitting and receiving an ultrasonic wave is constituted of a self-repairing material.

According to another aspect of the present disclosure, there is provided an ultrasound endoscope including: an insertion portion inserted into a body of a subject; and an ultrasound transducer including: a plurality of piezoelectric devices, each of the plurality of piezoelectric devices being configured to emit an ultrasonic wave according to an electrical signal input thereto, and convert an incident ultrasonic wave from an outside into an electrical signal; and an outer surface in which a material of a scanning surface transmitting and receiving an ultrasonic wave is constituted of a self-repairing material, wherein the ultrasound transducer is provided at a distal end of the insertion portion.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, forms to implement the present disclosure (hereinafter, embodiments) will be described wither reference to the drawings. Embodiments described below are not intended to limit the present disclosure. Furthermore, identical reference symbols are assigned to identical components throughout the drawings.

Schematic Configuration of Endoscope System

Figure 1:
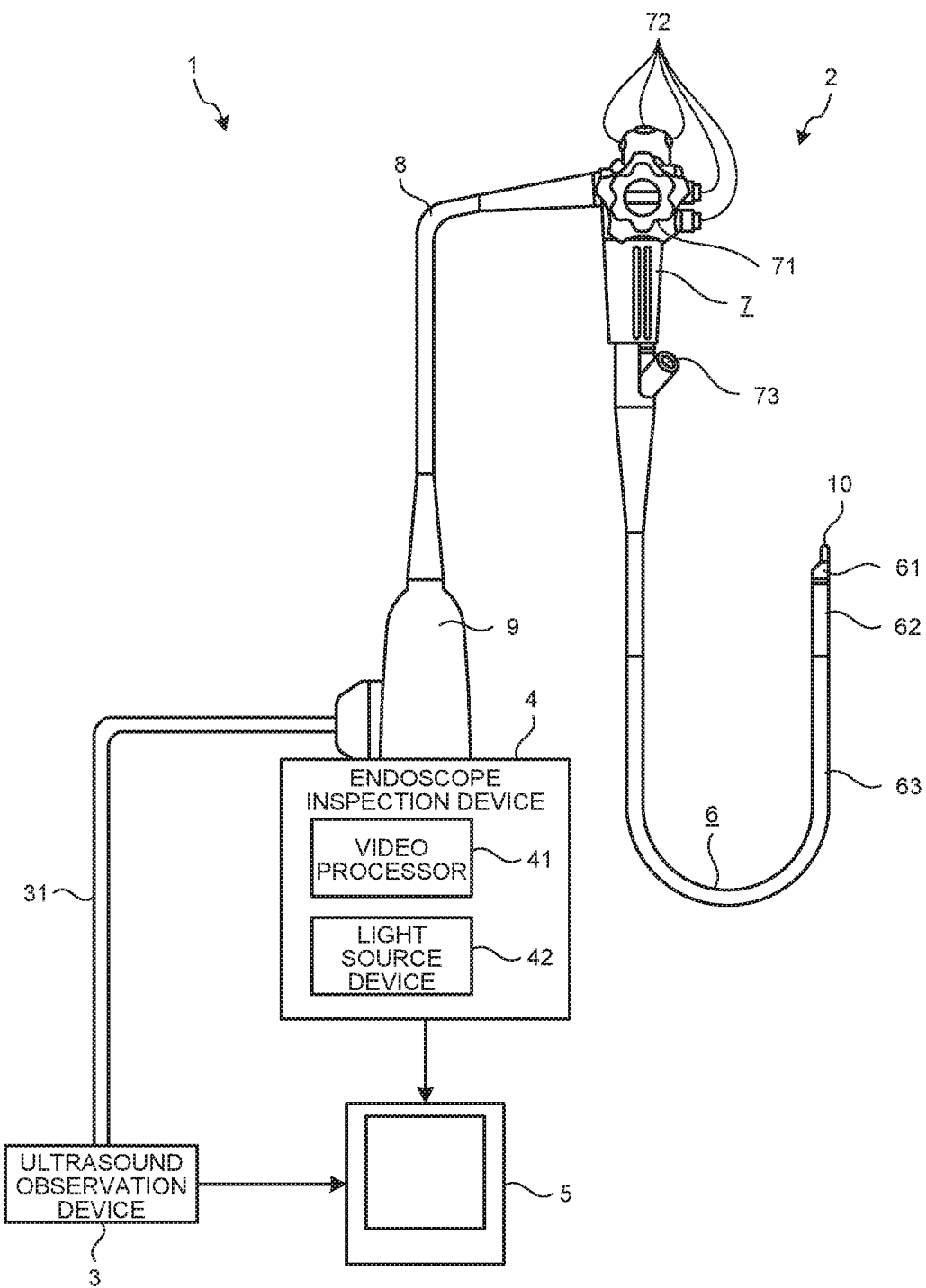
FIG. 1 illustrates an endoscope system according to a first embodiment.

FIG. 1 illustrates an endoscope system 1 according to a first embodiment.

The endoscope system 1 is a system to perform ultrasound diagnosis and treatment inside a body of a subject, such as a human, by using an ultrasound endoscope. This endoscope system 1 includes, as illustrated in FIG. 1, an ultrasound endoscope 2, an ultrasound observation device 3, an endoscope inspection device 4, and a display device 5.

The ultrasound endoscope 2 is structured such that a portion thereof is insertable into the body of the subject, and has a function of transmitting an ultrasonic pulse (acoustic pulse) toward a body wall in the inside of the subject and receiving an ultrasound echo reflected on the body of the subject to transmit an echo signal, and a function of imaging the inside of the body of the subject and outputting an image signal.

Detailed functions of the ultrasound endoscope 2 will be described later.

The ultrasound observation device 3 is electrically connected to the ultrasound endoscope 2 through an ultrasound cable 31 (FIG. 1), and outputs a pulse signal to the ultrasound endoscope 2 through the ultrasound cable 31, and receives an echo signal from the ultrasound endoscope 2. The ultrasound observation device 3 subjects the echo signal to predetermined processing to generate an ultrasound image.

To the endoscope inspection device 4, an endoscope connector 9 (FIG. 1) described later of the ultrasound endoscope 2 is detachably connected. This endoscope inspection device 4 includes a video processor 41 and a light source device 42 as illustrated in FIG. 1.

The video processor 41 receives an image signal from the ultrasound endoscope 2 through the endoscope connector 9. The video processor 41 subjects the image signal to predetermined processing to generate an endoscopic image.

The light source device 42 provides illumination light to illuminate the inside of the body of the subject to the ultrasound endoscope 2 through the endoscope connector 9.

The display device 5 is structured using a liquid crystal or an organic electroluminescence (EL), a cathode ray tube (CRT), or a projector, and displays an ultrasound image generated by the ultrasound observation device 3, an endoscopic image generated by the endoscope inspection device 4, and the like.

Configuration of Ultrasound Endoscope

Next, a configuration of the ultrasound endoscope 2 will be explained.

The ultrasound endoscope 2 includes, as illustrated in FIG. 1, an insertion portion 6, an operation portion 7, a universal cord 8, and the endoscope connector 9.

Figure 2:
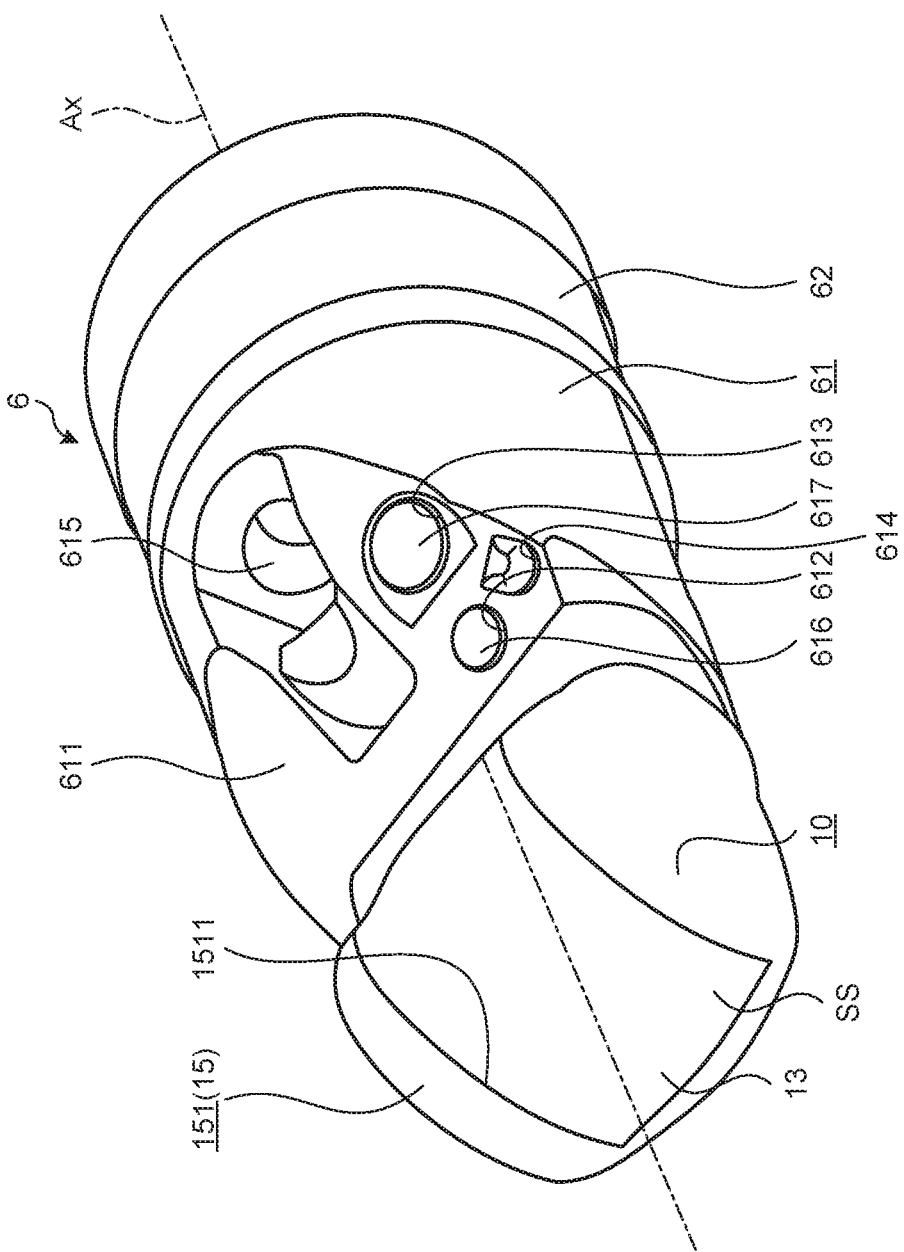
FIG. 2 is a perspective view illustrating a distal end of an insertion portion.

FIG. 2 is a perspective view illustrating a distal end of the insertion portion 6.

In the following, in explaining a structure of the insertion portion 6, a distal end side (distal end side in a direction of insertion into the body of a subject) of the insertion portion 6 is denoted simply as "distal end side", and a proximal end side (side on a direction apart from a distal end of the insertion portion 6) of the insertion portion is denoted simply as "proximal end".

The insertion portion is a portion to be inserted into the body of the subject. This insertion portion 6 includes, as illustrated in FIG. 1 or FIG. 2, an ultrasound transducer 10 arranged on the distal end side, a rigid member 61 that is connected to a proximal end side of the ultrasound transducer 10, a bendable portion 62 that is bendable and that is connected to the proximal end side of the ultrasound transducer 10, and a flexible tube 63 (FIG. 1) that is connected to a proximal end side of the bendable portion 62 and that has flexibility.

Inside the insertion portion 6, the operation portion 7, the universal cord 8, and the endoscope connector 9, a light guide (not illustrated) that transmits illumination light provided by the light source device 42, a transducer cable that transmits the pulse signal and the echo signal described above, and a signal cable (not illustrated) that transmits an image signal are routed, and a tubular channel (not illustrated) to let fluid flow through is arranged.

The rigid member 61 is a rigid member formed with a resin material or the like, and has a substantially cylindrical shape that extends along an insertion axis Ax (FIG. 2). The insertion axis Ax is an axis along a direction in which the insertion portion 6 stretches.

In this rigid member 61, an inclined surface 611 that makes the rigid member 61 tapered toward a distal end is formed on an outer circumferential surface on the distal end side.

In the rigid member 61, as illustrated in FIG. 2, an attachment hole (not illustrated) that is pierced through from a proximal end to a distal end, an illumination hole 612, an imaging hole 613, an air/water feed hole 614, a treatment tool channel 615, and the like that is pierced through from the proximal end to the inclined surface 611 are formed.

The attachment hole (not illustrated) described above is a hole in which the ultrasound transducer 10 is attached. Inside the attachment hole, the transducer cable (not illustrated) described above is inserted through.

Inside the illumination hole 612, an emitting end of the light guide (not illustrated) described above, and an illumination lens 616 (FIG. 2) to illuminate the illumination light emitted from the emitting end of the light guide to the inside of the body of the subject are arranged.

Inside the imaging hole 613, an object optical system 617 (FIG. 2) that collects light irradiated to the inside of the body of the subject and reflected on the inside of the body of the subject (subject image), and an imaging device (not illustrated) that captures a subject image collected by the object optical system 617 are arranged. An image signal captured by the imaging device is transmitted to the endoscope inspection device 4 (video processor 41) through the signal cable (not illustrated) described above.

In the first embodiment, the illumination hole 612 and the imaging hole 613 are formed on the inclined surface 611 as described above. Therefore, the ultrasound endoscope 2 according to the first embodiment is configured as an oblique endoscope that observes a direction intersecting the insertion axis Ax at an acute angle.

The air/water feed hole 614 is constitutes a part of the tubular channel (not illustrated) described above, and is a hole to feed air and water to the imaging hole 613 to clean an outer surface of the object optical system 617.

The treatment tool channel 615 is a path to let a treatment tool (not illustrated), such as a puncture needle, inserted inside the insertion portion 6 stick out therethrough to an outside.

The operation portion 7 is connected to the proximal end side of the insertion portion 6, and is a portion that receives various kinds of operations from a doctor, or the like. This operation portion 7 includes, as illustrated in FIG. 1, a bending knob 71 to operate and bend the bendable portion. 62, and plural operating members 72 to perform various kinds of operations.

Moreover, in the operation portion 7, a treatment-tool insertion inlet 73 (FIG. 1) that communicates with the treatment tool channel 615 through a tube (not illustrated) arranged inside the bendable portion 62 and the flexible tube 63, to insert a treatment tool (not illustrated) into the tube is arranged.

The universal cord 8 extends from the operation portion 7, and is a cord in which the light guide (not illustrated) described above, the transducer cable (not illustrated) described above, the signal cable (not illustrated) described above, and the tube (not illustrated) constituting a part of the tubular channel (not illustrated) described above are arranged.

The endoscope connector 9 is arranged at an end portion of the universal cord 8.

The endoscope connector 9 connects the ultrasound cable 31, and is connected to the video processor 41 and the light source device 42 by being inserted to the endoscope inspection device 4.

Configuration of Ultrasound Transducer

Next, a configuration of the ultrasound transducer 10 will be explained.

Figure 3:
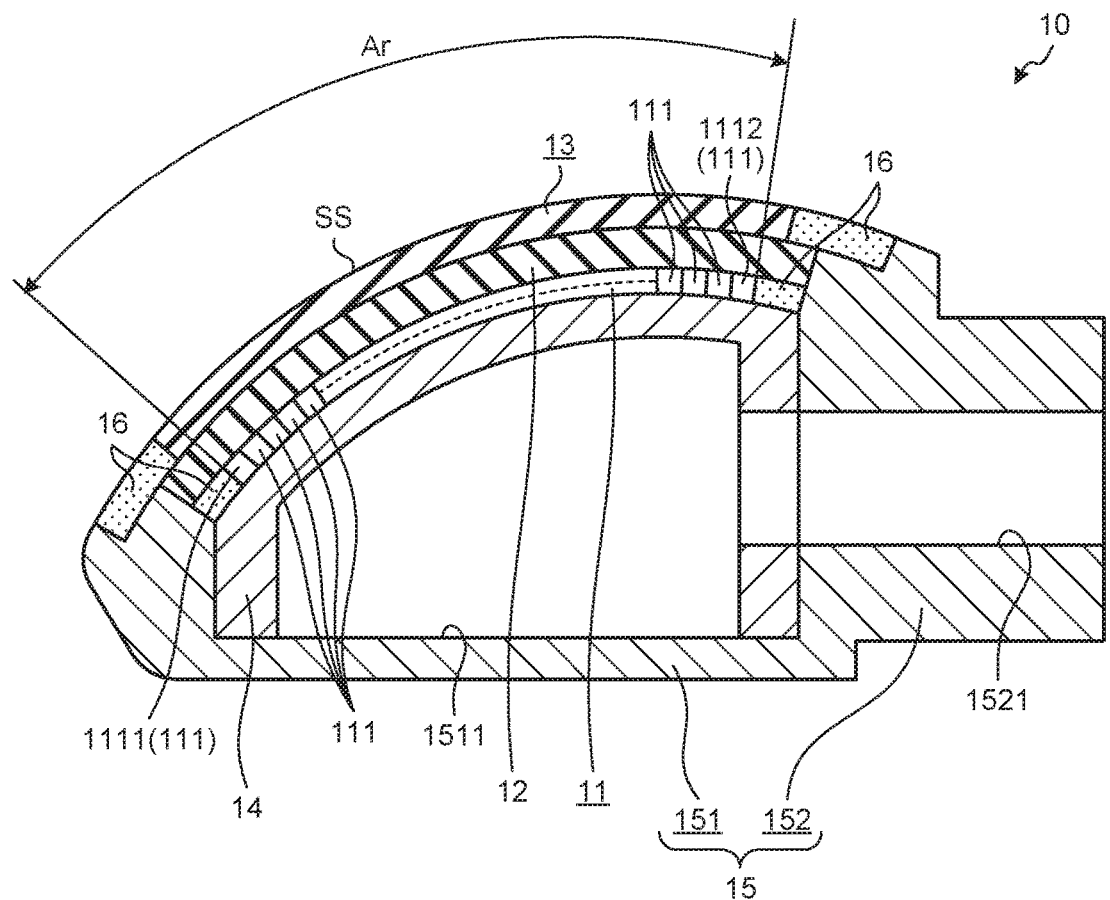
FIG. 3 is a cross-section illustrating an ultrasound transducer.

FIG. 3 is a cross-section illustrating the ultrasound transducer 10. Specifically, FIG. 3 is a cross-section of the ultrasound transducer 10 cut on a plane including the insertion axis Ax and perpendicular to a scanning surface SS.

The ultrasound transducer 10 is a convex ultrasound transducer, and has the scanning surface SS having a cylindrical surface convex toward the outside (upper side in FIG. 3). The scanning surface SS constitutes a part of an outer surface of the ultrasound transducer 10.

In the following, in explaining a structure of the ultrasound transducer 10, a circumferential direction of the scanning surface SS of the cylindrical surface is simply denoted as "circumferential direction", and a direction along a cylindrical axis in the scanning surface SS having the cylindrical surface (direction perpendicular to a page surface in FIG. 3) is denoted as "width direction".

The ultrasound transducer 10 scans (transceives) an ultrasound wave along the circumferential direction in an ultrasound transceiving area Ar (FIG. 3) in a fan shape on the cross section formed by a normal of the scanning surface SS.

This ultrasound transducer 10 includes, as illustrated in FIG. 3, a vibrating unit 11, an acoustic matching layer 12, an acoustic lens 13, a backing material 14, and a holding member 15.

The vibrating unit 11 is constituted of plural piezoelectric devices 111 as illustrated in FIG. 3.

The piezoelectric devices 111 are respectively structured with a long rectangular parallelepiped extending straight along the width direction, and are regularly aligned along the circumferential direction as illustrated in FIG. 3. Furthermore, on an outer surface of the piezoelectric device 111, the pair of electrodes are formed, although specific illustration thereof is omitted. The piezoelectric device 111 converts a pulse signal (corresponding to an electrical signal according to the present disclosure) input through the transducer cable (not illustrated) described above and the pair of electrodes (not illustrated) into an ultrasonic pulse, to transmit to the subject. Moreover, the piezoelectric device 111 converts an ultrasound echo reflected on the body of the subject into an electrical echo signal (corresponding to an electrical signal according to the present disclosure) expressing by voltage change, to output to the pair of electrodes (not illustrated) described above through the transducer cable (not illustrated) described above.

That is, in the ultrasound transceiving area Ar, a position of one end in the circumferential direction corresponds to a position of a piezoelectric device 1111 (FIG. 3) positioned at on end in the circumferential direction out of the piezoelectric devices 111. Moreover, a position of the other end in the circumferential direction corresponds to a position of a piezoelectric device 1112 (FIG. 3) positioned at the other end in the circumferential direction out of the piezoelectric devices 111.

The piezoelectric device 111 is formed by using PMN-PT single crystal, PMN-PZT single crystal, PZN-PT single crystal, PIN-PZN-PT single crystal, or a relaxer material.

The PMN-PT single crystal is short form of solid solution of magnesium niobate and lead titanate. The PMN-PZT single crystal is short form of solid solution of magnesium niobite and lead zirconate titanate. The PZN-PT single crystal is short form of solid solution of lead zinc niobate and lead titanium. The PZN-PT single crystal is short form of solid solution of lead zinc niobate and lead titanate. The PIN-PZN-PT single crystal is short form of solid solution of lead indium niobate, lead zinc niobate, and lead titanium. The relaxer material is general term of a three-component piezoelectric material that is lead zirconate titanate (PZT) doped with lead compound perovskite, which is a relaxer material, to increase the piezoelectric constant and the permittivity. The lead compound perovskite is expressed by $Pb(B1, B2)O_3$, and B1 is either magnesium, zinc, indium, or scandium, and B2 is either niobium, tantalum, or tungsten. These materials have excellent piezoelectric effect. Therefore, even when it is miniaturized, the electrical impedance value may be maintained low, and it is preferable from the viewpoint of the impedance matching between the pair of electrodes (not illustrated) described above.

The acoustic matching layer 12 extends along the circumferential direction as illustrated in FIG. 3, and is layered on a side of the outer surface of the ultrasound transducer 10 (upper side in FIG. 3) relative to the vibrating unit 11. The acoustic matching layer 12 matches acoustic impedances of the vibrating unit 11 and the body of the subject to effectively transmit sound (ultrasonic wave) between the vibrating unit 11 (piezoelectric device 111) and the body of the subject.

The acoustic lens 13 is fixed, as illustrated in FIG. 3, on an outer surface side of the ultrasound transducer 10 relative to the acoustic matching layer 12 by adhesion of an adhesive (not illustrated) or by tight coupling force produced when casting a lens material itself. That is, in the acoustic lens 13, a surface on an upper side in FIG. 3 is to be the scanning surface SS. This scanning surface OS has an arc-shaped cross-section extending along the circumferential direction, an arc-shaped cross-section extending along the width direction, and a convex shape that projects outward. The acoustic lens 13 converges ultrasonic pulses transmitted from the vibrating unit 11 through the acoustic matching layer 12. Moreover, the acoustic lens 13 transmits ultrasound echo reflected on the body of the subject to the acoustic matching layer 12.

A material of the acoustic lens 13 includes a self-repairing material. Details of the self-repairing material will be described later.

The backing material 14 is arranged to sandwich the vibrating unit 11 with the acoustic matching layer 12 as illustrated in FIG. 3, and is a member that attenuates unnecessary ultrasonic vibrations generated by actions of the piezoelectric devices 111. This backing material 14 is formed by using a material having a high attenuation factor, such as an epoxy resin in which a filler of alumina, zirconia, a tungsten, or the like is dispersed, and a rubber in which the filler described above is dispersed.

The holding member 15 includes a holding portion 151 and an attaching portion 152 as illustrated in FIG. 3.

The holding portion 151 is a portion that holds a unit in which the vibrating unit 11, the acoustic matching layer 12, the acoustic lens 13, and the backing material 14 are integrated. In this holding portion 151, a concave portion 1511 that exposes the scanning surface SS of the acoustic lens 13 to the outside while holding the unit is formed therein as illustrated in FIG. 3. In a gap between the concave portion 1511 and the unit, an adhesive 16 (FIG. 3) is filled.

The attaching portion 152 is formed integrally with a proximal end of the holding portion 151, and is a portion that is inserted into the attachment hold (not illustrated) in the rigid member 61 described above to be attached to the rigid member 61. In this attaching portion 152, a insertion hole 1521 that is pierced through to the concave portion 1511 from a proximal end, and in which the transducer cable (not illustrated) described above is inserted through is formed.

About Self-Repairing Material Forming Acoustic Lens 13

Next, the self-repairing material that forms the acoustic lens 13 will be described.

Figure 4:
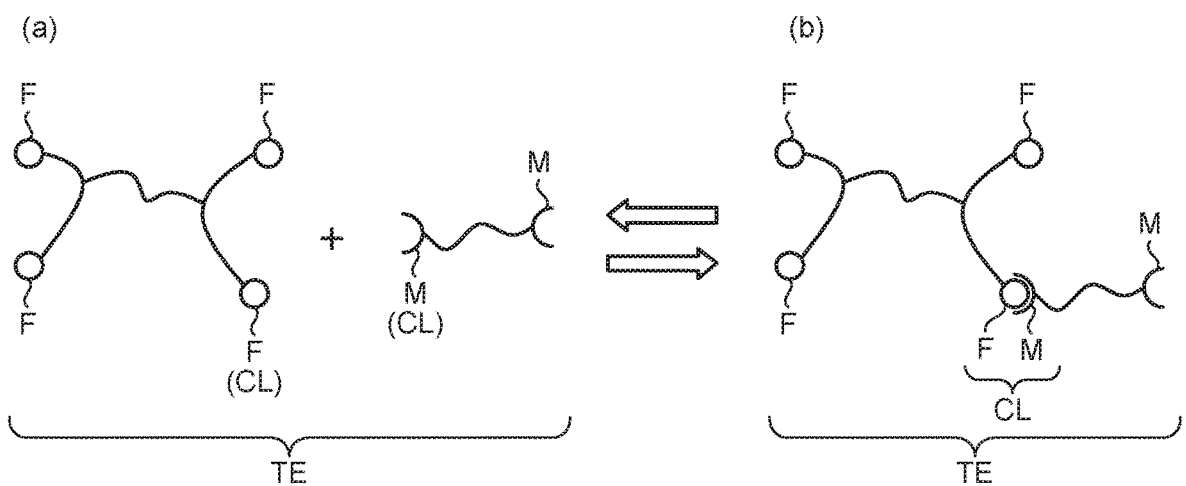
FIG. 4 illustrates properties of a self-repairing material that constitutes an acoustic lens.

FIG. 4 illustrates properties of the self-repairing material that constitutes the acoustic lens 13.

In the first embodiment, as the self-repairing material constituting the acoustic lens 13, thermoplastic elastomer TE that forms a cross-linking structure CL between furan F and maleimide M by Diels-Alder reaction is used as illustrated in FIG. 4.

As the thermoplastic elastomer TE, "1,1'-(methylenedi-1, 4-phenylene) bismaleimide-furfuryl glycidyl ether-Jeffamine 4000" may be exemplified.

In the thermoplastic elastomer TE, the cross-linking structure CL proceeds cross-linking ((b) in FIG. 4) and uncross-linking ((a) in FIG. 4) reversibly according to temperature.

Specifically, a case in which the scanning surface SS of the acoustic lens 13 is damaged (cut or the like) is assumed.

In this case, at a damaged portion, the cross-linking structure CL is a uncross-linked state. When the acoustic lens 13 is heated to, for example, about 80° and let it stand at the temperature, the cross-linking structure CL other than the cross-linking structure CL that has been in the uncross-linked state due to the damage also becomes the uncross-linked state by the retro-Diel-Alder reaction. Therefore, the thermoplastic elastomer TE (furan F and maleimide M) have fluidity. When the temperature of the acoustic lens 13 is gradually decreased to about 25°, furan F and maleimide M in the uncross-linked state become the cross-linked state by Diels-Alder reaction. As a result, the damage is repaired.

The thermoplastic elastomer TE according to the present disclosure is preferable to satisfy conditions (1) to (8) below by changing content of materials (for example, a content of furan F).

(1) It is durable to withstand general cleaning, sanitation, and sterilization processes of an endoscope.
(2) The acoustic impedance is approximately 1.0 MRayl to 2.0 MRayl (approximately $1.0 \times 10^6$ kg/(m²·s) to $2.0 \times 10^6$ kg/(m²·s)).

It is ideal that the acoustic impedance of the acoustic lens 13 takes a value between the acoustic impedance of a living body (water) and the acoustic impedance of the acoustic matching layer 12, or is the same value as a living body (water). Furthermore, if the above condition (2) is satisfied, reflection of ultrasonic wave on a boundary between the acoustic lens 13 and the body of the subject (living body) may be made small. That is, the propagation efficiency of ultrasonic waves may be improved.

(3) The longitudinal wave velocity is approximately 900 m/s to 1200 m/s.

In the acoustic lens 13, refraction is caused by a difference in longitudinal wave velocity from a living body (water), and a lens effect may be obtained. To form the acoustic lens 13 in a convex shape convenient to contact a living body, it is necessary to be slower than the acoustic velocity of water, 1500 m/s. Therefore, it is preferable to satisfy the above condition (3).

(4) The attenuation factor is 10 dB/(cm·MHz) or smaller.

If the above condition (4) is satisfied, attenuation of ultrasonic wave when passing through the acoustic lens 13 may be made small. That is, the propagation efficiency of ultrasonic waves may be improved.

(5) A predetermined shape may be formed by molding or injection molding, and the contraction factor at that time is 10% or smaller.

To increase the accuracy of focal length of the acoustic lens 13, the precision of a curvature radius in a curved portion is important. Moreover, to transfer the shape of a molding precisely, the contraction factor is necessary to be small. If the above condition (5) is satisfied, the shape of the acoustic lens may be precisely formed.

(6) The hardness is Shore A>50.

If the above condition (6) is satisfied, strength as high as not to be scratched or ripped may be obtained.
(7) It has an insulation property of 4 kV or higher at the thickness of approximately 0.15 mm.

If the above condition (7) is satisfied, electrical safety may be assured.
(8) It has biocompatibility.

If the above condition (8) is satisfied, safety when applied to a human body may be assured.

According to the first embodiment described above, following effects are produced.

In the ultrasound transducer 10 according to the first embodiment, the acoustic lens 13 constitutes the scanning surface SS out of the outer surface of the ultrasound transducer 10, and is constituted of a self-repairing material.

Therefore, for example, even when the scanning surface SS is damaged (cut, or the like) by a treatment tool, such as a puncture needle sticking out through the treatment tool channel 615, the damage may be self-repaired. In other words, because the damage is self-repaired, the scanning surface SS is not prone to having dirt adhered thereon, and adequate ultrasound images may be constantly acquired.

Moreover, it is not necessary to replace the ultrasound transducer 10 itself, and it will not take long time for repairment.

Therefore, according to the ultrasound transduces 10 according to the first embodiment, convenience may be improved.

Next, a second embodiment will be described.

In the following explanation, identical reference symbols are assigned to components identical to the first embodiment described above, and detailed explanation thereof is omitted or simplified.

The second embodiment differs only in a point that a material different from the material explained in the first embodiment described above is used as the self-repairing material constituting the acoustic lens 13.

Figure 5:
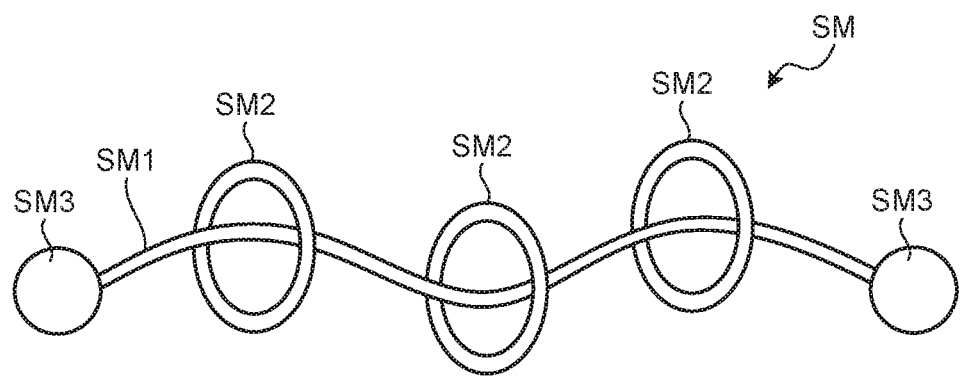
FIG. 5 illustrates properties of a self-repairing material that constitutes an acoustic lens according to a second embodiment.
Figure 6:
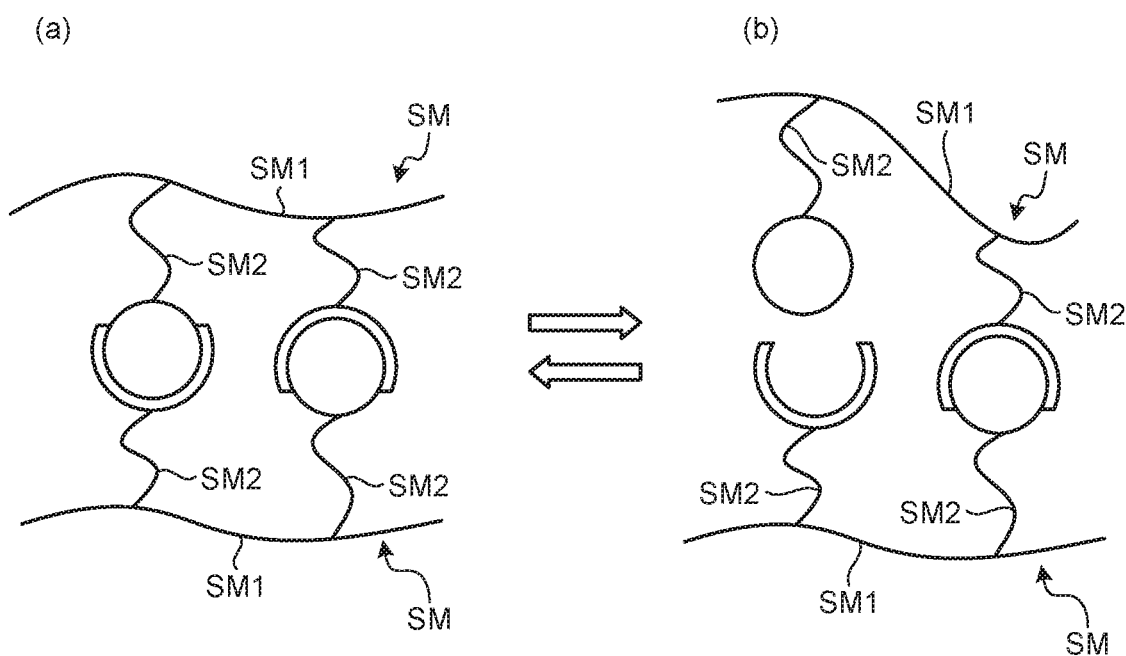
FIG. 6 illustrates properties of the self-repairing material that constitutes an acoustic lens.

FIG. 5 and FIG. 6 illustrate properties of a self-repairing material that constitutes the acoustic lens 13 according to the second embodiment.

In the second embodiment, as the self-repairing material constituting the acoustic lens 13, polyrotaxane (supermolecular polymer) SM illustrated in FIG. 5 is used.

Polyrotaxane SM includes a string-like polymer SM1, many of ring molecules SM2, and a pair of stopper molecules SM3.

The string-like polymer SM1 is constituted of, for example, polyethylene glycol.

The ring molecule SM2 is constituted of, for example cyclodextrine. The string-like polymer SM1 threads the many ring molecules therethrough.

The stopper molecule SM3 is constituted of, for example, adamantylamine. The pair of stopper molecules SM3 are arranged at both ends of the string-like polymer SM1, and prevent the ring molecules SM2 from dethreading from the string-like polymer SM1.

The ring molecules SM2 is movable freely along the string-like polymer SM1, and proceeds cross-linking ((a) in FIG. 6) and uncross-linking ((b) in FIG. 6) reversibly between itself and the other ring molecule SM2 of the polyrotaxane SM.

Specifically, a case in which the scanning surface SS of the acoustic lens 13 is damaged (cut or the like) is assumed.

In this case, at a damaged portion, the ring molecules SM2 that have been in the cross-linked state become the uncross-linked state. Because the ring molecules SM2 may move freely along the string-like polymer SM1, when separated pieces of the polyrotaxane SM are in contact with each other, one of the ring molecules SM2 of the polyrotaxane SM in the uncross-linked state and the other ring molecule SM2 of the polyrotaxane SM become the cross-linked state. As a result, the damage is repaired.

The polyrotaxane SM according to the present disclosure is preferable to satisfy the conditions (1) to (8) explained in the first embodiment by changing a content of the material (for example, content of the ring molecule SM2).

As in the second embodiment described above, also when the polyrotaxane SM is used as the self-repairing material constituting the acoustic lens 13, an effect similar to that of the first embodiment describe above is produced.

Next, a third embodiment will be described.

In the following explanation, identical reference symbols are assigned to components identical to the first embodiment described above, and detailed explanation thereof is omitted or simplified.

Figure 7:
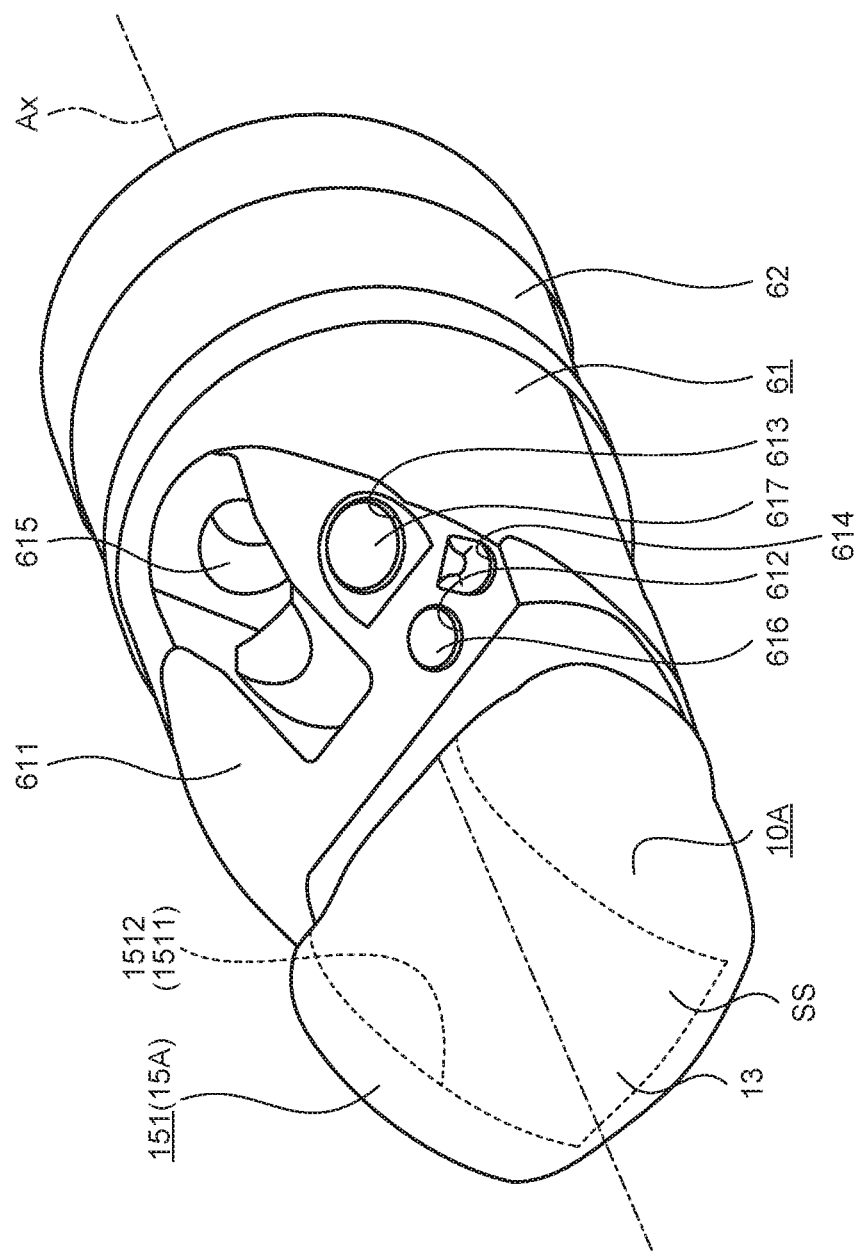
FIG. 7 illustrates an ultrasound transducer according to a third embodiment.
Figure 8:
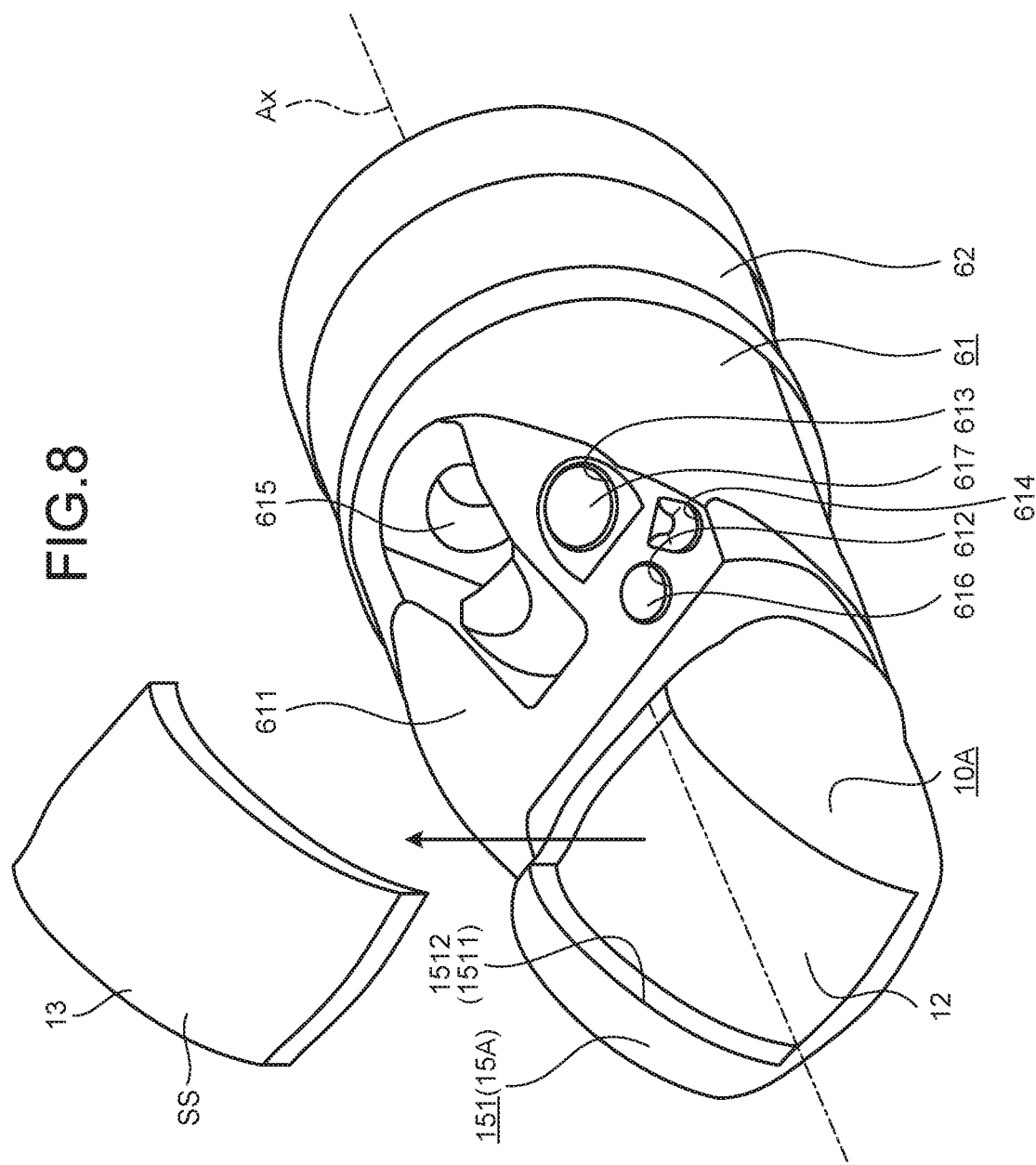
FIG. 8 illustrates an ultrasound transducer according to the third embodiment.

FIG. 7 and FIG. 8 illustrate an ultrasound transducer 10A according to the third embodiment. Specifically, FIG. 7 and FIG. 8 are drawings corresponding to FIG. 2.

The third embodiment differs only in a point that a holding member 15A constituted of a different material from the holding member 15 is used in the ultrasound transducer 10 explained in the first embodiment described above.

Specifically, the holding member 15 is constituted of the thermoplastic elastomer TE, which is a self-repairing material, similarly to the acoustic lens 13. It is preferable that the holding member 15A be made to have the hardness higher than the acoustic lens 13 by changing a content of the thermoplastic elastomer TE (for example, content of furan F). Furthermore, the holding member ISA includes the holding portion 151 and the attaching portion 152, similarly to the holding member 15 explained in the above first embodiment.

In the holding portion 151, the concave portion 1511 and an opening portion 1512 (FIG. 7) have substantially the same shape as a shape of a rim of the acoustic lens 13. The opening portion 1512 corresponds to a contact portion according to the present disclosure. The acoustic lens 13 is heated to, for example, about 80°, in a state being engaged in the opening portion 1512, and then cooled to about 25°. Thus, the cross-linking structure CL is formed between furan F and maleimide M by Diels-Alder reaction, and a rim portion of the acoustic lens 13 and the opening portion 1512 are thereby joined to each other. The joint portion is indicated by a broken line in FIG. 7. That is, the acoustic lens 13 according to the third embodiment is not fixed to the acoustic matching layer 12, but fixed to the holding member 15A.

Moreover, when the scanning surface SS of the acoustic lens 13 is damaged in a non-self-repairable manner by use of the ultrasound transducer 10A, the acoustic lens 13 is taken off (FIG. 8) along the broken line in FIG. 7, and a new piece of the acoustic lens 13 is engaged in the opening portion 1512. The new acoustic lens 13 is heated to, for example, about 80°, and then cooled to about 25° similarly to the above description, and is joined to the opening portion 1512 as the cross-linking structure CL is formed between furan F and maleimide M by Diels-Alder reaction.

According to the third embodiment explained above, following effects are produced in addition to effects similar to those of the first embodiment described above.

In the ultrasound transducer 10A according to the third embodiment, the holding member 15A is constituted of a self-repairing material, and joined to the acoustic lens 13. Therefore, even when the scanning surface SS is damaged in a non-self-repairable manner, only the acoustic lens 13 may be replaced easily.

The present disclosure has been described above, but the present disclosure is not to be limited only to the first to the third embodiments described above.

In the first to the third embodiments described above, the ultrasound transducers 10, 10A are constituted of a convex ultrasound transducer, but at is not limited thereto, and may be constituted of a radial ultrasound transducer.

In the first to the third embodiments described above, the endoscope system 1 has both the function of generating an ultrasound image and the function of generating an endoscopic image, but it is not limited thereto, and may be configured to have only the function of generating an ultrasound image.

In the first to the third embodiments described above, not limited to the medical field, the endoscope system 1 may be an endoscope system that observes the inside of a subject, such as a mechanical structure in an industrial field.

In the first to the third embodiments described above, the ultrasound endoscope 2 is constituted of an oblique endoscope that observes a direction intersecting the insertion axis Ax at an acute angle, but it is not limited thereto, and may be configured as a side view endoscope that observes a direction intersecting the insertion axis Ax at a right angle.

In the first to the third embodiments described above, the scanning surface SS that transmits and receives an ultrasonic wave out of the outer surface of the ultrasound transducers 10, 10A is constituted of the acoustic lens 13, but it is not limited thereto. For example, the acoustic lens 13 may be formed with a silicone resin or the like, and a protection portion (coating layer) that constitutes the scanning surface SS and that is made from the self-repairing material explained in the first and the second embodiments described above may be arranged on a surface on an outer surface side of the acoustic lens 13. Moreover, for example, the acoustic lens 13 is omitted, and a protection portion (coating layer) that constitutes the scanning surface SS and that is made from the self-repairing material explained in the first and the second embodiments described above may be arranged on a surface on an outer surface side of the acoustic matching layer 12. Furthermore, for example, the acoustic lens 13 and the acoustic matching layer 12 are omitted, and a protection portion (coating layer) that constitutes the scanning surface SS and that is made from the self-repairing material explained in the first and the second embodiments described above may be arranged on a surface on an outer surface side of the vibrating unit 11.

When the acoustic lens 13 is formed with silicone resin or the like, and the protection portion (coating layer) is arranged on the surface of the outer surface side of the acoustic lens 13, the protection portion is preferable to satisfy conditions (9) to (11) below.

(9) The acoustic impedance is approximately 1.0 MRayl to 2.0 MRayl ($1.0 \times 10^6$ to $2.0 \times 10^6$ kg/(m²·s).

It is ideal that the acoustic impedance of the protection portion takes a value between the acoustic impedance of the acoustic lens 13 and the acoustic impedance of a living body (water), or the same value as that of a living body (water). If the above condition (9) is satisfied, reflection of an ultrasonic wave on a boundary between the acoustic lens 13—the protection portion—the living body may be made small. That is, the propagation efficiency of an ultrasonic wave may be improved.

(10) The thickness is uniform.

If the above condition (10) is satisfied, a refraction effect of the acoustic lens 13 is not inhibited.

(11) The attenuation factor is 10 dB/(cm·MHz) or smaller together with the acoustic lens 13.

If the above condition (11) is satisfied, propagation of ultrasonic wave is not inhibited.

In the first to the third embodiments described above, as the self-repairing material according to the present disclosure, the thermoplastic elastomer TE or the polyrotaxane SM is used, but it is not limited thereto. As long as it is a self-repairing material, other materials (for example, resin, adhesive, wax, or the like having thermoplasticity) may be used.

In the third embodiment described above, the holding member 15A is constituted of the thermoplastic elastomer TE, but it is not limited thereto, and may be constituted of the polyrotaxane SM, similarly to the second embodiment described above. Moreover, it may be structure such that only the opening portion. 1512 is constituted of the thermoplastic elastomer TE or the polyrotaxane SM.

According to the ultrasound transducer and the ultrasound endoscope according to the present disclosure, an effect of increasing convenience is produced.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound transducer comprising:
   a plurality of piezoelectric devices, each of the plurality of piezoelectric devices being configured to emit an ultrasonic wave according to an electrical signal input thereto, and to convert an incident ultrasonic wave from an outside into an electrical signal; and
   an acoustic lens provided on a scanning surface for transmitting and receiving an ultrasonic wave, the acoustic lens being configured to:
      radiate the ultrasonic wave emitted from the plurality of piezoelectric devices to the outside; and
      transmit the incident ultrasonic wave from the outside to the plurality of piezoelectric devices,
   wherein the acoustic lens comprises a self-repairing material, and
   the self-repairing material includes a cross-linking structure wherein cross-linking and uncross-linking of the cross-linking structure proceed reversibly in the cross-linking structure so as to repair a damaged portion without affecting acoustic characteristics.

2. The ultrasound transducer according to claim 1, further comprising
   a housing comprising a recess having an opening, the housing being configured to house the piezoelectric devices and the acoustic lens in the recess, wherein an edge of the opening of the housing is a contact surface configured to contact the acoustic lens, and the contact surface comprises a self-repairing material, and the contact surface being configured to be joined to the acoustic lens.

3. The ultrasound transducer according to claim 1, wherein the self-repairing material includes a thermoplastic elastomer in which a cross-linking structure is formed between furan and maleimide by Diels-Alder reaction, and
   cross-linking and uncross-linking proceed reversibly according to temperature in the cross-linking structure.

4. The ultrasound transducer according to claim 1, wherein the self-repairing material includes polyrotaxane having a structure in which multiple ring molecules are threaded through a string-like polymer, and
   cross-linking and uncross-linking proceed reversibly in the ring molecules.

5. An ultrasound endoscope comprising:
   an insertion portion inserted into a body of a subject; and
   an ultrasound transducer provided at a distal end of the insertion portion, the ultrasound transducer comprising:
      a plurality of piezoelectric devices, each of the plurality of piezoelectric devices being configured to emit an ultrasonic wave according to an electrical signal input thereto, and to convert an incident ultrasonic wave from an outside into an electrical signal; and
      an acoustic lens provided on a scanning surface for transmitting and receiving an ultrasonic wave, the acoustic lens being configured to:
         radiate the ultrasonic wave emitted from the plurality of piezoelectric devices to the outside; and
         transmit the incident ultrasonic wave from the outside to the plurality of piezoelectric devices,
      wherein the acoustic lens includes a self-repairing material, and
      the self-repairing material includes a cross-linking structure wherein cross-linking and uncross-linking of the cross-linking structure proceed reversibly in the cross-linking structure so as to repair a damaged portion without affecting acoustic characteristics.

6. The ultrasound transducer according to claim 1, wherein an acoustic impedance of the self-repairing material is 1.0 MRayl to 2.0 MRayl.

7. The ultrasound transducer according to claim 1, wherein longitudinal wave velocity of the self-repairing material is 900 m/s to 1200 m/s.

8. The ultrasound transducer according to claim 1, wherein an attenuation factor of the self-repairing material is 10 dB/(cmMHz) or smaller.

9. The ultrasound transducer according to claim 1, wherein the acoustic lens is formed by molding, and a contraction factor at a time of the molding is 10% or smaller.

10. The ultrasound transducer according to claim 1, wherein Shore A hardness of the self-repairing material is greater than 50.

11. The ultrasound transducer according to claim 1, wherein the self-repairing material has an insulation property of 4 kV or higher at a thickness of 0.15 mm.

12. The ultrasound transducer according to claim 1, wherein the self-repairing material has biocompatibility.

13. The ultrasound transducer according to claim 1, wherein
   the acoustic lens comprises:
      a main body layer; and
      a protection layer covering an outer surface of the main body layer; and
   the protection layer is the scanning surface and formed of the self-repairing material.

* * * * *